United States Patent
Sugahara et al.

(10) Patent No.: US 11,529,613 B2
(45) Date of Patent: *Dec. 20, 2022

(54) ORGANIC MATTER DECOMPOSITION CATALYST, ORGANIC MATTER DECOMPOSITION AGGREGATE, AND ORGANIC MATTER DECOMPOSITION APPARATUS

(71) Applicant: Murata Manufacturing Co., Ltd., Nagaokakyo (JP)

(72) Inventors: Nario Sugahara, Nagaokakyo (JP); Kentaro Ishihara, Nagaokakyo (JP); Satoshi Kuretake, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 286 days.

This patent is subject to a terminal disclaimer.

(21) Appl. No.: 16/678,078

(22) Filed: Nov. 8, 2019

(65) Prior Publication Data

US 2020/0070130 A1    Mar. 5, 2020

Related U.S. Application Data

(63) Continuation of application No. PCT/JP2018/045261, filed on Dec. 10, 2018.

(30) Foreign Application Priority Data

May 11, 2018  (JP) .............................. JP2018-092386

(51) Int. Cl.
   *B01J 23/889* (2006.01)
   *A61L 9/03* (2006.01)
   (Continued)

(52) U.S. Cl.
   CPC ............ *B01J 23/8892* (2013.01); *A61L 9/03* (2013.01); *B01D 53/865* (2013.01);
   (Continued)

(58) Field of Classification Search
   None
   See application file for complete search history.

(56) References Cited

U.S. PATENT DOCUMENTS 3,644,147 A    2/1972  Young, II
5,380,692 A    1/1995  Nakatsuji et al.
(Continued)

FOREIGN PATENT DOCUMENTS

JP    H0780310 A      3/1995
JP    2000140635 A    5/2000
(Continued)

OTHER PUBLICATIONS

International Search Report issued for PCT/JP2018/045261, dated Feb. 5, 2019.
(Continued)

*Primary Examiner* — Colin W. Slifka
(74) *Attorney, Agent, or Firm* — ArentFox Schiff LLP

(57) ABSTRACT

An organic matter decomposition catalyst that contains a perovskite type complex oxide represented by $A_xB_yM_zO_w$, wherein A contains 90 at % or more of at least one element selected from the group consisting of Ba and Sr, B contains 80 at % or more of Zr, M is at least one element selected from the group consisting of Mn, Co, Ni, and Fe, y+z=1, x>1, z<0.4, and w is a positive value that satisfies electrical neutrality.

19 Claims, 4 Drawing Sheets

(51) Int. Cl.
*B01D 53/86* (2006.01)
*B01J 23/00* (2006.01)
*B01J 23/34* (2006.01)
*B01J 23/68* (2006.01)
*B01J 23/78* (2006.01)
*B01J 35/10* (2006.01)
*C01G 45/12* (2006.01)
*C01G 51/00* (2006.01)
*C01G 53/00* (2006.01)
*B01J 21/06* (2006.01)
*B01J 35/04* (2006.01)
*B01D 53/94* (2006.01)
*B01J 21/04* (2006.01)
*B01J 35/02* (2006.01)
*B01J 37/00* (2006.01)
*B01J 21/16* (2006.01)

(52) U.S. Cl.
CPC ..... *B01D 53/8668* (2013.01); *B01D 53/8687* (2013.01); *B01D 53/8696* (2013.01); *B01D 53/94* (2013.01); *B01J 21/04* (2013.01); *B01J 21/066* (2013.01); *B01J 23/002* (2013.01); *B01J 23/34* (2013.01); *B01J 23/688* (2013.01); *B01J 23/78* (2013.01); *B01J 35/026* (2013.01); *B01J 35/04* (2013.01); *B01J 35/1009* (2013.01); *B01J 35/1038* (2013.01); *B01J 35/1061* (2013.01); *B01J 35/1066* (2013.01); *B01J 35/1071* (2013.01); *B01J 35/1076* (2013.01); *C01G 45/125* (2013.01); *C01G 45/1207* (2013.01); *C01G 51/66* (2013.01); *C01G 53/66* (2013.01); *B01D 2255/104* (2013.01); *B01D 2255/2042* (2013.01); *B01D 2255/2047* (2013.01); *B01D 2255/2061* (2013.01); *B01D 2255/2063* (2013.01); *B01D 2255/2073* (2013.01); *B01D 2255/2092* (2013.01); *B01D 2255/2094* (2013.01); *B01D 2255/20707* (2013.01); *B01D 2255/20715* (2013.01); *B01D 2255/20738* (2013.01); *B01D 2255/20746* (2013.01); *B01D 2255/20753* (2013.01); *B01D 2255/20792* (2013.01); *B01D 2255/402* (2013.01); *B01D 2255/9202* (2013.01); *B01D 2255/9207* (2013.01); *B01D 2257/7027* (2013.01); *B01D 2258/01* (2013.01); *B01D 2258/02* (2013.01); *B01J 21/16* (2013.01); *B01J 37/009* (2013.01); *C01P 2002/34* (2013.01); *C01P 2002/50* (2013.01); *C01P 2002/72* (2013.01); *C01P 2002/77* (2013.01); *C01P 2006/12* (2013.01); *C01P 2006/14* (2013.01); *C01P 2006/16* (2013.01)

(56) References Cited

U.S. PATENT DOCUMENTS

| | | | |
|---|---|---|---|
| 6,060,420 | A | 5/2000 | Munakata et al. |
| 8,123,931 | B2 | 2/2012 | Kang et al. |
| 8,329,612 | B2 | 12/2012 | Sato et al. |
| 8,569,200 | B2 | 10/2013 | Kang et al. |
| 2002/0035035 | A1 | 3/2002 | Kirchnerova et al. |
| 2007/0027031 | A1 | 2/2007 | Ikeda et al. |
| 2007/0249497 | A1 | 10/2007 | Tanaka et al. |
| 2009/0108239 | A1 | 4/2009 | Caro et al. |
| 2009/0131252 | A1 | 5/2009 | Tanaka et al. |
| 2009/0286677 | A1 | 11/2009 | Takeshima et al. |
| 2009/0286680 | A1 | 11/2009 | Hirano et al. |
| 2010/0139152 | A1 | 6/2010 | Hucul et al. |
| 2012/0074357 | A1 | 3/2012 | Sato et al. |
| 2016/0115835 | A1 | 4/2016 | Daido et al. |

FOREIGN PATENT DOCUMENTS

| | | |
|---|---|---|
| JP | 3406001 B2 | 5/2003 |
| JP | 2006231280 A | 9/2006 |
| JP | 2006346603 A | 12/2006 |
| JP | 2006347825 A | 12/2006 |
| JP | 5076377 B2 | 11/2012 |
| JP | 2013244479 A | 12/2013 |
| JP | 2015229137 A | 12/2015 |
| JP | 6036276 B2 | 11/2016 |
| WO | 0016900 A1 | 3/2000 |
| WO | 2004096436 | 11/2004 |
| WO | 2005058490 A1 | 6/2005 |
| WO | 2010143676 A1 | 12/2010 |
| WO | 2014189115 A1 | 11/2014 |
| WO | 2015194451 A1 | 12/2015 |

OTHER PUBLICATIONS

Kirchenerova, J. et al.; "Design criteria for high-temperature combustion catalysts"; Catalysis Letters, Jul. 2000, vol. 67, No. 2-4, pp. 175-181.
Tuyen, Nguyen Van et al.; Interaction of Hydrogen with Perovskite-supported Metal Catalysts: I. M/Sr$_{1-x}$Zr$_{1-y}$O$_{3-\alpha}$ (M = CU, Pd); Kinetics and Catalysts, 1996, vol. 37, No. 4, pp. 575-578.
Written Opinion of the International Searching Authority issued for PCT/JP2019/017674, dated Jul. 16, 2019.
Written Opinion of the International Searching Authority issued for PCT/JP2019/015483, dated Jul. 16, 2019.
Written Opinion of the International Searching Authority issued for PCT/JP2019/008592, dated May 21, 2019.
Written Opinion of the International Searching Authority issued for PCT/JP2019/008593, dated May 21, 2019.
Written Opinion of the International Searching Authority issued for PCT/JP2018/045261, dated Feb. 5, 2019.
Japanese Office Action issued for Japanese Application No. 2020-518162, dated Jun. 29, 2021.
International Search Report issued for PCT/JP2019/017674, dated Jul. 16, 2019.
International Search Repori issued for PCT/JP2019/015483, dated Jul. 16, 2019.
International Search Report issued for PCT/JP2019/008592, dated May 21, 2019.
International Search Report issued for PCT/JP2019/008593, dated May 21, 2019.
Gallucci, Katia, et al.; "Catalytic combustion of methane on Ba Zr$_{(1-x)}$Me$_x$O$_3$ perovskites synthesised by a modified citrate method"; Catalysis Today, 197, (2012) (1), pp. 236-242.
Yuxi Liu et al.; "Controlled preparation and high catalytic performance of three-dimensionally ordered macroporous LaMnO3 with nanovoid skeletons for the combustion of toluene"; Journal of Catalysis 287, 2012, pp. 149-160.

ORGANIC MATTER DECOMPOSITION CATALYST, ORGANIC MATTER DECOMPOSITION AGGREGATE, AND ORGANIC MATTER DECOMPOSITION APPARATUS

CROSS REFERENCE TO RELATED APPLICATIONS

The present application is a continuation of International application No. PCT/JP2018/045261, filed Dec. 10, 2018, which claims priority to Japanese Patent Application No. 2018-092386, filed May 11, 2018, the entire contents of each of which are incorporated herein by reference.

FIELD OF THE INVENTION

The present invention relates to an organic matter decomposition catalyst used for decomposing an organic matter, an organic matter decomposition aggregate that is an aggregate of the organic matter decomposition catalyst, and an organic matter decomposition apparatus in which the organic matter decomposition aggregate is placed.

BACKGROUND OF THE INVENTION

Two types of apparatus are known conventionally as an organic matter decomposition apparatus for an organic matter-containing gas. One is a "direct combustion type" apparatus in which an organic matter is subjected to oxidative combustion directly at a high temperature of 800° C. or more by a burner or a heater. The other is a "catalytic combustion type" apparatus in which an organic matter is subjected to oxidative combustion at a low temperature less than 500° C. using oxidation action of a catalyst.

In general, the catalyst activity degrades through a long period of use in a catalytic combustion type organic matter decomposition apparatus. One of causes of the degradation is heat degradation due to exposure of the catalyst to a high temperature. The reason for the heat degradation is considered to be a decrease in the number of active sites caused by the progress of sintering or aggregation of the catalyst material. The word "active site" means a site where a reaction molecule of an organic matter is oxidized on the surface of the catalyst.

A degraded catalyst needs to be replaced with new one. From the viewpoint of extending the replacement life of the catalyst, the catalyst is desired to have good heat resistance.

The aforementioned organic matter decomposition apparatus can be used as a deodorization device. Recently, a hybrid type deodorization device is known in which a catalytic combustion type organic matter decomposition apparatus is placed in a subsequent stage of a direct combustion type organic matter decomposition apparatus for higher deodorization efficiency. In such a hybrid type deodorization device, it is necessary that the catalyst used in the catalytic combustion type organic matter decomposition apparatus in the subsequent stage be protected from the heat of the exhaust gas from the direct combustion type organic matter decomposition apparatus in the preceding stage. For the reason, a cooling mechanism such as an air mixing fan and a heat exchanger is usually placed in front of the catalytic combustion type apparatus.

The cooling mechanism is, however, desired to be omitted from the viewpoint of the installation space, cost, and the like. Therefore, the catalyst used in the catalytic combustion type organic matter decomposition apparatus in the subsequent stage is desired to be a heat resistant catalyst that can resist the heat of the exhaust gas from the direct combustion type organic matter decomposition apparatus in the preceding stage.

When the deodorization device is formed as an integrated hybrid device in which the catalyst is put into the direct combustion type organic matter decomposition apparatus directly, more advantages can be expected in the aspect of the installation space, cost, and the like. In that case, however, the catalyst is exposed to a high temperature of a burner and the like, so that higher heat resistance is required of the catalyst.

Because an oxidation decomposition reaction of an organic matter is generally exothermic, it is not enough to consider only the temperature of the environment where the catalyst is placed, but it is necessary to consider the rise in the catalyst temperature caused by the decomposition of an organic matter-containing gas at a high concentration. From this point of view, a heat resistant catalyst that hardly degrades at high temperatures is desired.

As aforementioned, high heat resistance is required of a catalyst, and Patent Document 1 discloses a catalyst that has good heat resistance, and hardly degrades even after a heat treatment at 800° C. for 100 hours.

Patent Document 1: Japanese Patent Application Laid-Open No. 2015-229137

SUMMARY OF THE INVENTION

A catalyst is, however, also expected to be used at a temperature higher than 800° C., so that the development of a catalyst that hardly degrades in a heat treatment at a high temperature is desired.

The present invention is intended to solve the aforementioned problem, and an object of the present invention is to provide a catalyst that hardly degrades in a heat treatment at a high temperature, an organic matter decomposition aggregate that is an aggregate of the catalyst, and an organic matter decomposition apparatus in which the organic matter decomposition aggregate is placed.

An organic matter decomposition catalyst according to the present invention is an organic matter decomposition catalyst used for decomposing an organic matter and contains a perovskite type complex oxide represented by general formula $A_xB_yM_zO_w$, wherein A contains 90 at % or more of at least one element selected from the group consisting of Ba and Sr, B contains 80 at % or more of Zr, M is at least one element selected from the group consisting of Mn, Co, Ni, and Fe, x, y, and z satisfy relationships of $y+z=1$, $x>1$, and $z<0.4$, and w is a positive value that satisfies electrical neutrality.

x may preferably satisfy a relationship of $x<1.1$.

z may preferably satisfy a relationship of $z>0.02$.

x and z respectively may preferably satisfy relationships of $1.001 \leq x \leq 1.05$ and $0.05 \leq z \leq 0.2$.

A may preferably further contain at least one element selected from the group consisting of Y, La, Lu, Ca, and Ag.

B may preferably further contain at least one element selected from the group consisting of Mg, Zn, Al, Ga, Sc, In, Ge, Ti, Hf, Sn, Nb, and Ta.

An organic matter decomposition aggregate according to the present invention is an organic matter decomposition aggregate of the aforementioned organic matter decomposition catalyst, and has a specific surface area of 6 m²/g or more.

In the aforementioned organic matter decomposition aggregate, x may preferably satisfy a relationship of x≥1.005.

An organic matter decomposition apparatus according to the present invention includes: a tube in which an organic matter flows; a heating unit that heats the organic matter flowing in the tube; and a control unit that controls the heating unit, and in the apparatus, the aforementioned organic matter decomposition aggregate is placed in an area heated by the heating unit inside the tube.

The control unit may control the heating unit so that the area heated by the heating unit may preferably have a temperature of 700° C. or more.

The control unit may control the heating unit so that the organic matter decomposition aggregate may preferably have a temperature of 700° C. or more.

The control unit may control the heating unit so that the organic matter decomposition aggregate may preferably have a temperature of 1500° C. or less.

The organic matter decomposition catalyst according to the present invention contains a perovskite type complex oxide represented by general formula $A_xB_yM_zO_w$, wherein A contains 90 at % or more of at least one element selected from the group consisting of Ba and Sr, B contains 80 at % or more of Zr, M is at least one element selected from the group consisting of Mn, Co, Ni, and Fe, x, y, z, and w in general formula $A_xB_yM_zO_w$ satisfy relationships of y+z=1, x>1, and z<0.4, and w is a positive value that satisfies electrical neutrality. The degradation of the composition can be suppressed in a heat treatment at a high temperature of, for example, more than 1000° C.

The organic matter decomposition aggregate according to the present invention is an organic matter decomposition aggregate of the aforementioned organic matter decomposition catalyst, and has a specific surface area of 6 m²/g or more, so that the organic matter decomposition aggregate can reduce the degradation in a heat treatment at a high temperature of, for example, more than 1000° C. and improve the decomposition rate of the organic matter.

In the organic matter decomposition apparatus according to the present invention, the aforementioned organic matter decomposition aggregate is placed, so that the replacement cycle of the organic matter decomposition aggregate can be lengthened by using the organic matter decomposition aggregate that hardly degrades in a heat treatment at a high temperature of, for example, more than 1000° C.

DETAILED DESCRIPTION OF PREFERRED EMBODIMENTS OF THE INVENTION

Figure 1:
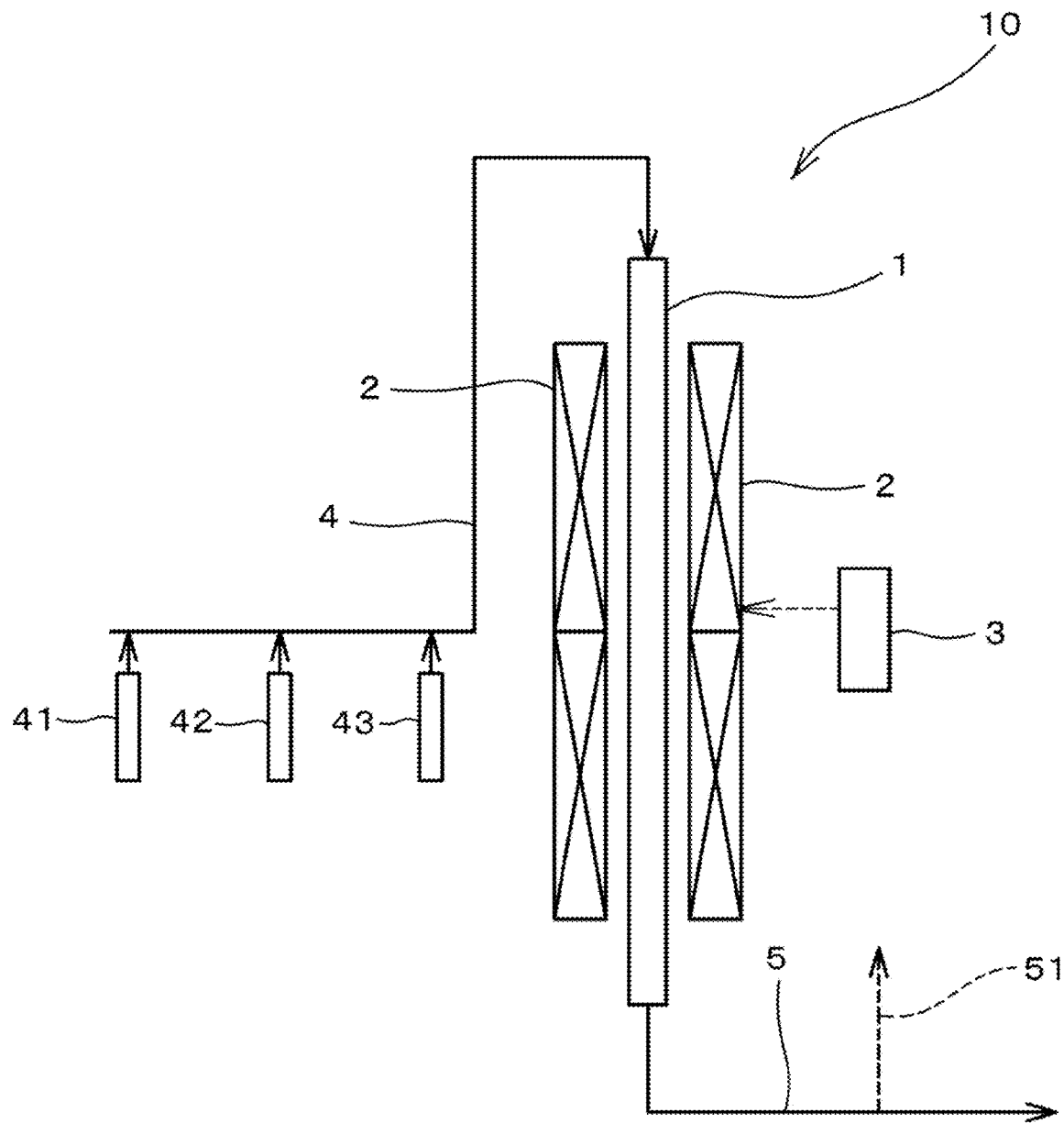
FIG. 1 is a diagram that shows a schematic constitution of a test apparatus used in a test to evaluate organic matter decomposition performance.

Features of the present invention will be specifically described below with reference to an embodiment of the present invention.

An organic matter decomposition catalyst according to the present invention satisfies the following requirements (hereinafter referred to as the "requirements of the present invention"). That is, the organic matter decomposition catalyst according to the present invention contains a perovskite type complex oxide represented by general formula $A_xB_yM_zO_w$, wherein A contains 90 at % or more of at least one element selected from the group consisting of Ba and Sr, B contains 80 at % or more of Zr, and M is at least one element selected from the group consisting of Mn, Co, Ni, and Fe. x, y, z, and w in general formula $A_xB_yM_zO_w$ satisfy the following relationships.

y+z=1
x>1
z<0.4
w is a positive value that satisfies electrical neutrality.

Example 1

High purity powders of $BaCO_3$, $SrCO_3$, $ZrO_2$, $MnCO_3$, $Co_3O_4$, NiO, and $Fe_2O_3$ were weighed so as to have the composition shown in Table 1, pure water was added to the resulting mixture, and the mixture was wet-mixed with a $ZrO_2$ boulder to obtain a slurry. The slurry was dried with a dryer at 120° C., and then the resulting powder was heat-treated under the conditions of 1100° C. for 2 hours to obtain a target perovskite type complex oxide.

The resulting perovskite type complex oxide, to which an organic binder and pure water were added, was wet-mixed with a $ZrO_2$ boulder to obtain a slurry. The slurry was dried with a dryer at 120° C. and then ground. After that, the resulting matter was molded using a compression molding machine into a cylinder having a diameter of 8.5 mm and a thickness of 8 mm.

The resulting molded body was fired under the conditions of 1050° C. for 2 hours and then ground with a mortar and classified to obtain a particulate organic matter decomposition catalyst having a size of 0.5 mm or more and 0.6 mm or less.

A part of the resulting organic matter decomposition catalyst was subjected to a high temperature heat treatment in an electric furnace under the conditions of 1200° C. for 3 hours, 1300° C. for 3 hours, and 1400° C. for 3 hours.

By the aforementioned steps, organic matter decomposition catalysts before and after the high temperature heat treatment, the catalysts respectively having compositions represented by sample numbers 1 to 35 shown in Table 1, were obtained.

TABLE 1

| Smpl # | Charge comp. ratio x | y | z | y + z | A(x) Ba | Sr | B(y) Zr | Mn | M(z) Co | Ni | Fe | Bf high temp | Toluene decomposition rate (%) 1200° C./3 h | 1300° C./3 h | 1400° C./3 h | Bf high temp | SSA (m2/g) 1200° C./3 h | 1300° C./3 h | 1400° C./3 h | Degr. rate (%) |
|---|---|---|---|---|---|---|---|---|---|---|---|---|---|---|---|---|---|---|---|---|
| 1* | 0.005 | 0.900 | 0.100 | 1.000 | 1.000 | | 1.000 | 1.000 | | | | 91.4 | 88.7 | 84.6 | 77.0 | 8.8 | 5.2 | 3.5 | 1.8 | 15.7 |
| 2* | 1.000 | 0.900 | 0.100 | 1.000 | 1.000 | | 1.000 | 1.000 | | | | 92.5 | 90.0 | 86.4 | 79.7 | 9.5 | 5.9 | 3.8 | 2.3 | 13.8 |
| 3 | 1.001 | 0.900 | 0.100 | 1.000 | 1.000 | | 1.000 | 1.000 | | | | 93.3 | 92.6 | 91.6 | 89.4 | 9.7 | 6.0 | 4.0 | 2.5 | 4.2 |
| 4 | 1.005 | 0.900 | 0.100 | 1.000 | 1.000 | | 1.000 | 1.000 | | | | 94.2 | 94.1 | 93.7 | 92.4 | 10.1 | 6.6 | 4.6 | 3.2 | 1.9 |
| 5 | 1.010 | 0.900 | 0.100 | 1.000 | 1.000 | | 1.000 | 1.000 | | | | 94.6 | 94.5 | 94.1 | 93.2 | 10.4 | 7.0 | 5.3 | 3.9 | 1.4 |
| 6 | 1.050 | 0.900 | 0.100 | 1.000 | 1.000 | | 1.000 | 1.000 | | | | 94.5 | 94.6 | 94.5 | 93.9 | 11.5 | 8.2 | 6.7 | 5.2 | 0.6 |
| 7 | 1.100 | 0.900 | 0.100 | 1.000 | 1.000 | | 1.000 | 1.000 | | | | 87.4 | 87.3 | 87.4 | 86.6 | 13.2 | 9.9 | 8.1 | 6.8 | 1.0 |
| 8 | 1.001 | 0.980 | 0.020 | 1.000 | 1.000 | | 1.000 | 1.000 | | | | 81.7 | 81.4 | 81.1 | 80.6 | 10.7 | 7.3 | 5.4 | 4.0 | 1.4 |
| 9 | 1.001 | 0.950 | 0.050 | 1.000 | 1.000 | | 1.000 | 1.000 | | | | 92.4 | 92.1 | 91.6 | 90.6 | 10.2 | 6.6 | 4.7 | 3.3 | 1.9 |
| 10 | 1.001 | 0.800 | 0.200 | 1.000 | 1.000 | | 1.000 | 1.000 | | | | 94.4 | 93.6 | 92.3 | 89.8 | 9.0 | 6.5 | 3.5 | 2.0 | 4.9 |
| 11* | 1.001 | 0.600 | 0.400 | 1.000 | 1.000 | | 1.000 | 1.000 | | | | 93.1 | 88.4 | 83.4 | 76.0 | 8.2 | 4.5 | 2.5 | 1.0 | 18.4 |
| 12 | 1.050 | 0.980 | 0.020 | 1.000 | 1.000 | | 1.000 | 1.000 | | | | 86.7 | 86.5 | 86.6 | 86.2 | 12.7 | 9.3 | 7.8 | 6.2 | 0.6 |
| 13 | 1.050 | 0.950 | 0.050 | 1.000 | 1.000 | | 1.000 | 1.000 | | | | 93.4 | 93.4 | 93.3 | 92.9 | 12.3 | 8.8 | 7.4 | 5.7 | 0.5 |
| 14 | 1.050 | 0.800 | 0.200 | 1.000 | 1.000 | | 1.000 | 1.000 | | | | 94.9 | 94.7 | 94.3 | 92.9 | 10.5 | 7.2 | 5.7 | 4.2 | 2.1 |
| 15* | 1.050 | 0.600 | 0.400 | 1.000 | 1.000 | | 1.000 | 1.000 | | | | 94.1 | 91.7 | 88.1 | 81.1 | 9.2 | 5.6 | 4.0 | 2.5 | 13.9 |
| 16* | 1.000 | 0.900 | 0.100 | 1.000 | 1.000 | | 1.000 | 1.000 | | | | 91.3 | 89.4 | 86.1 | 80.0 | 7.8 | 5.5 | 4.0 | 2.3 | 12.4 |
| 17 | 1.001 | 0.900 | 0.100 | 1.000 | 1.000 | | 1.000 | 1.000 | | | | 91.6 | 90.9 | 89.4 | 87.1 | 7.9 | 5.4 | 4.1 | 2.5 | 4.9 |
| 18 | 1.005 | 0.900 | 0.100 | 1.000 | 1.000 | | 1.000 | 1.000 | | | | 92.1 | 91.8 | 91.0 | 89.9 | 8.4 | 5.7 | 4.5 | 3.2 | 2.4 |
| 19 | 1.006 | 0.800 | 0.200 | 1.000 | 1.000 | | 1.000 | 1.000 | | | | 93.5 | 92.8 | 91.5 | 90.3 | 8.0 | 5.1 | 3.7 | 2.0 | 3.4 |
| 20* | 1.005 | 0.600 | 0.400 | 1.000 | 1.000 | | 1.000 | 1.000 | | | | 93.3 | 90.6 | 86.4 | 79.2 | 7.0 | 4.6 | 2.9 | 1.1 | 15.1 |
| 21* | 1.000 | 0.900 | 0.100 | 1.000 | 1.000 | | 1.000 | 0.400 | 0.400 | 0.100 | 0.100 | 89.6 | 87.5 | 83.6 | 77.3 | 8.8 | 5.3 | 3.6 | 2.1 | 13.7 |
| 22 | 1.001 | 0.900 | 0.100 | 1.000 | 1.000 | | 1.000 | 0.400 | 0.400 | 0.100 | 0.100 | 90.1 | 88.8 | 86.4 | 83.8 | 8.9 | 5.5 | 3.8 | 2.3 | 8.1 |
| 23 | 1.005 | 0.900 | 0.100 | 1.000 | 1.000 | | 1.000 | 0.400 | 0.400 | 0.100 | 0.100 | 90.9 | 90.2 | 89.1 | 87.9 | 9.3 | 6.1 | 4.4 | 3.0 | 3.3 |
| 24 | 1.005 | 0.800 | 0.200 | 1.000 | 1.000 | | 1.000 | 0.400 | 0.400 | 0.100 | 0.100 | 92.1 | 90.9 | 89.8 | 87.6 | 8.6 | 5.2 | 3.5 | 1.9 | 4.9 |
| 25* | 1.005 | 0.600 | 0.400 | 1.000 | 1.000 | | 1.000 | 0.400 | 0.400 | 0.100 | 0.100 | 91.5 | 87.4 | 82.1 | 75.5 | 7.2 | 4.5 | 2.6 | 1.0 | 17.5 |
| 26* | 1.000 | 0.900 | 0.100 | 1.000 | 1.000 | | 1.000 | 1.000 | | | | 85.6 | 83.5 | 79.8 | 73.5 | 9.6 | 5.8 | 3.9 | 2.1 | 14.1 |
| 27 | 1.001 | 0.900 | 0.100 | 1.000 | | 1.000 | 1.000 | 1.000 | | | | 86.1 | 84.9 | 82.5 | 79.5 | 9.8 | 6.0 | 4.0 | 2.5 | 7.7 |
| 28 | 1.005 | 0.900 | 0.100 | 1.000 | | 1.000 | 1.000 | 1.000 | | | | 87.1 | 86.4 | 85.2 | 83.9 | 10.8 | 6.5 | 4.2 | 2.7 | 3.7 |
| 29 | 1.005 | 0.800 | 0.200 | 1.000 | | 1.000 | 1.000 | 1.000 | | | | 90.5 | 89.2 | 88.3 | 86.2 | 9.7 | 5.9 | 3.8 | 2.1 | 4.8 |
| 30* | 1.005 | 0.600 | 0.400 | 1.000 | | 1.000 | 1.000 | 1.000 | | | | 88.6 | 84.6 | 80.0 | 73.1 | 8.6 | 4.6 | 2.9 | 1.2 | 17.5 |
| 31* | 1.000 | 0.900 | 0.100 | 1.000 | 0.500 | 0.500 | 1.000 | 0.700 | 0.200 | 0.050 | 0.050 | 89.9 | 87.2 | 83.9 | 78.2 | 9.0 | 5.4 | 3.5 | 2.2 | 13.0 |
| 32 | 1.001 | 0.900 | 0.100 | 1.000 | 0.500 | 0.500 | 1.000 | 0.700 | 0.200 | 0.050 | 0.050 | 90.4 | 89.2 | 87.4 | 85.6 | 9.0 | 5.5 | 3.6 | 2.4 | 5.3 |
| 33 | 1.005 | 0.900 | 0.100 | 1.000 | 0.500 | 0.500 | 1.000 | 0.700 | 0.200 | 0.050 | 0.050 | 91.7 | 90.7 | 89.0 | 88.5 | 9.4 | 5.8 | 3.9 | 2.6 | 3.5 |
| 34 | 1.005 | 0.800 | 0.200 | 1.000 | 0.500 | 0.500 | 1.000 | 0.700 | 0.200 | 0.050 | 0.050 | 93.4 | 92.3 | 91.2 | 89.1 | 9.0 | 5.4 | 3.5 | 2.2 | 4.6 |
| 35* | 1.005 | 0.600 | 0.400 | 1.000 | 0.500 | 0.500 | 1.000 | 0.700 | 0.200 | 0.050 | 0.050 | 92.1 | 88.2 | 84.0 | 77.1 | 8.5 | 4.8 | 2.7 | 1.1 | 16.6 |

<Test to Evaluate Organic Matter Decomposition Performance>

(1) Test Apparatus

FIG. 1 is a diagram that shows a schematic constitution of a test apparatus 10 used in the test to evaluate the organic matter decomposition performance of the organic matter decomposition catalyst. The test apparatus 10 includes a tube 1 in which an organic matter flows, a heating unit 2 that heats the organic matter flowing in the tube 1, and a control unit 3 that controls the heating unit 2.

The organic matter decomposition aggregate that is an aggregate of the organic matter decomposition catalyst produced by the aforementioned method is placed in an area heated by the heating unit 2 inside the tube 1.

A gas supply tube 4 is connected to the upstream side of the tube 1. To the gas supply tube 4, a toluene supply line 41 to supply toluene (an organic matter), a nitrogen supply line 42 to supply nitrogen ($N_2$), and an oxygen supply line 43 to supply oxygen ($O_2$) are connected. That is, the tube 1 is supplied with a gas to be treated containing toluene, nitrogen, and oxygen via the gas supply tube 4.

To the downstream side of the tube 1, a gas exhaust tube 5 to exhaust the treated gas, which is obtained after the decomposition of the organic matter in the tube 1 to the outside of the system, is connected. To the gas exhaust tube 5, a sampling line 51 to sample the treated gas is connected. The gas exhaust tube 5 and the sampling line 51 are configured to analyze the toluene concentration in the treated gas by a gas chromatograph.

The control unit 3 is configured to control the heating unit 2 so that the area heated by the heating unit 2 may have a temperature of, for example, 700° C. or more and 1500° C. or less.

The control unit 3 is also configured to control the heating unit 2 so that the organic matter decomposition aggregate may have a temperature of 700° C. or more and 1500° C. or less. By controlling the heating unit 2 so that the organic matter decomposition aggregate may have the temperature of 700° C. or more, the catalyst activity of the organic matter decomposition aggregate can be enhanced. Moreover, by controlling the heating unit 2 so that the organic matter decomposition aggregate may have the temperature of 1500° C. or less, the degradation of the organic matter decomposition aggregate can be suppressed.

(2) Test Method

The central portion of the tube 1 in the test apparatus 10 shown in FIG. 1 was filled with the organic matter decomposition aggregate that is the aggregate of the aforementioned organic matter decomposition catalyst, and the tube 1 was continuously supplied with the gas to be treated containing toluene, nitrogen, and oxygen to perform the toluene decomposition test. The composition of the gas to be treated was 50 ppm of toluene ($C_7H_8$), 80 vol % of nitrogen ($N_2$), and 20 vol % of oxygen ($O_2$), the gas flow velocity in the measurement was 0.4 m/s, the space velocity (SV) was 150000 (/h), and the catalyst temperature was 300° C.

The treated gas was sampled at the outlet of the sampling line 51, and the toluene concentration was determined by analysis using a gas chromatograph. The toluene decomposition rate was determined based on the following formula (1).

Toluene decomposition rate (%)=100−100×(toluene concentration/50)     (1)

The toluene decomposition rates of the organic matter decomposition catalysts represented by sample numbers 1 to 35 are shown in Table 1. The toluene decomposition rates were determined using the organic matter decomposition catalysts before the high temperature heat treatment, after the high temperature heat treatment at 1200° C. for 3 hours, after the high temperature heat treatment at 1300° C. for 3 hours, and after the high temperature heat treatment at 1400° C. for 3 hours.

Then, the BET specific surface area (SSA) ($m^2/g$) of each of the organic matter decomposition aggregates was measured using a full automatic BET specific surface area analyzer (Macsorb HM model-1201 manufactured by Mountech Co., Ltd.) under a degassing condition of 400° C. for 20 minutes. The BET specific surface areas (SSA) were measured using the organic matter decomposition aggregates before the high temperature heat treatment, after the high temperature heat treatment at 1200° C. for 3 hours, after the high temperature heat treatment at 1300° C. for 3 hours, and after the high temperature heat treatment at 1400° C. for 3 hours.

Then, to determine the heat resistance, a degradation rate was calculated based on the following formula (2) using the toluene decomposition rate of the organic matter decomposition catalyst before the high temperature heat treatment and the toluene decomposition rate of the organic matter decomposition catalyst after the high temperature heat treatment at 1400° C. for 3 hours.

Degradation rate (%)=100−100×(toluene decomposition rate after high temperature heat treatment at 1400° C.)/(toluene decomposition rate before high temperature heat treatment)     (2)

Samples represented by the sample numbers 1, 2, 11, 15, 16, 20, 21, 25, 26, 30, 31, and 35 with * mark shown in Table 1 are organic matter decomposition catalysts that do not satisfy the requirements of the present invention.

As shown in Table 1, the organic matter decomposition catalysts represented by the sample numbers without * mark, which satisfy the requirements of the present invention, had high toluene decomposition rates before the high temperature heat treatment, after the high temperature heat treatment at 1200° C. for 3 hours, after the high temperature heat treatment at 1300° C. for 3 hours, and after the high temperature heat treatment at 1400° C. for 3 hours. Moreover, the degradation rates were lower than 10%.

In contrast, the organic matter decomposition catalysts represented by the sample numbers with * mark, which do not satisfy the requirements of the present invention, had low toluene decomposition rates especially after the high temperature heat treatment at 1400° C. for 3 hours, and the degradation rates are 10% or higher.

That is, the organic matter decomposition catalyst according to the present invention has a high toluene decomposition rate even after the high temperature heat treatment at 1400° C. for 3 hours, and is prevented from the heat degradation.

Among the organic matter decomposition catalysts represented by sample numbers 1 to 35, the organic matter decomposition catalysts represented by sample numbers 1 to 7 contain a perovskite type complex oxide represented by $A_xB_yM_zO_w$, wherein A is Ba, B is Zr, M is Mn, y=0.9, and z=0.1. In particular, concerning the organic matter decomposition catalysts represented by sample numbers 1 to 7, relationships were checked among the conditions in the high temperature heat treatment, the BET specific surface area, and the toluene decomposition rate.

Figure 2:
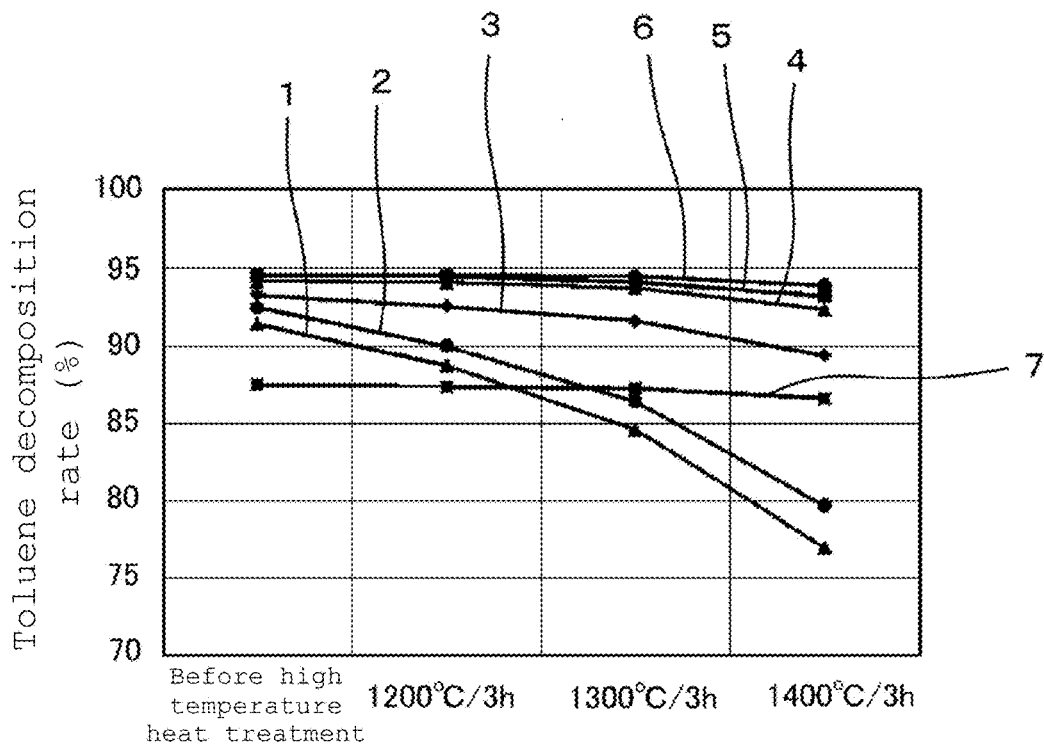
FIG. 2 is a graph that shows a relationship between heat treatment conditions and the toluene decomposition rate of catalysts represented by sample numbers 1 to 7.
Figure 3:
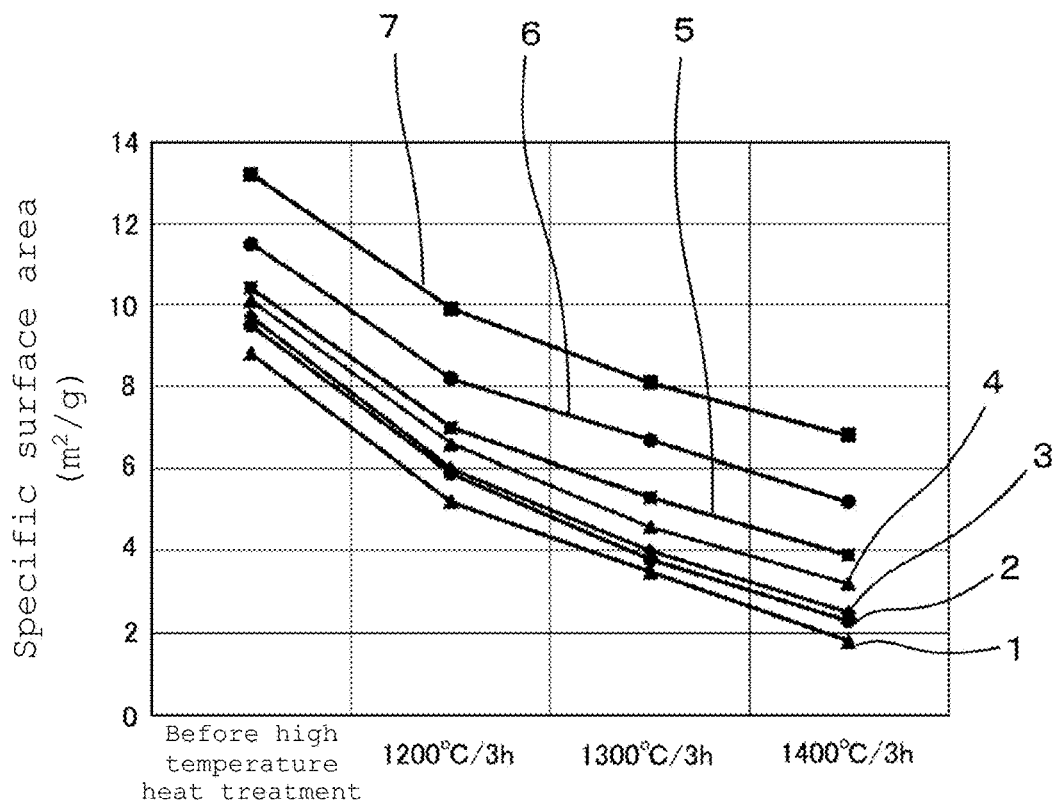
FIG. 3 is a graph that shows a relationship between heat treatment conditions and the BET specific surface area (SSA) of catalysts represented by sample numbers 1 to 7.
Figure 4:
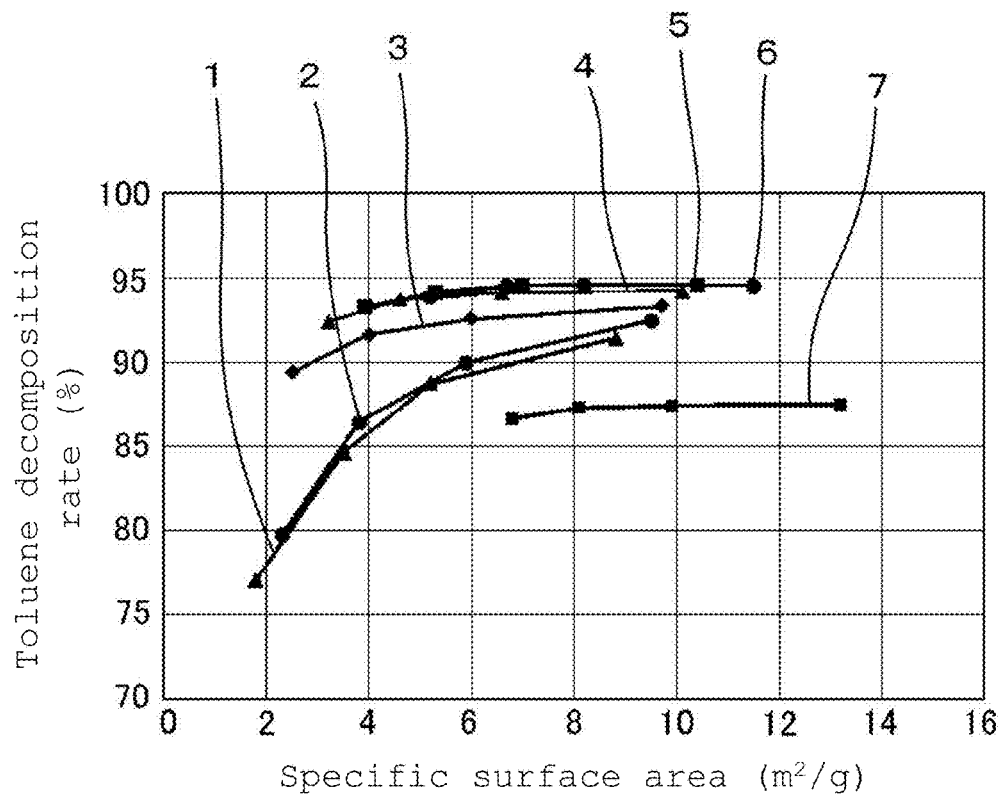
FIG. 4 is a graph that shows a relationship between the BET specific surface area (SSA) and the toluene decomposition rate of catalysts represented by sample numbers 1 to 7.
Figure 5:
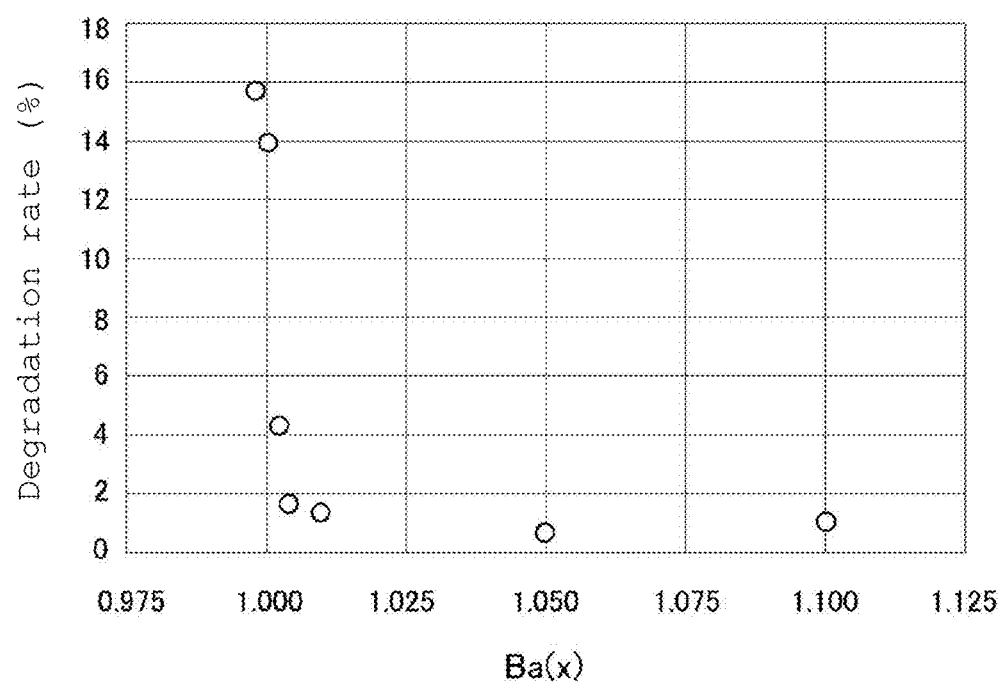
FIG. 5 is a graph that shows a relationship between the Ba content rate x and the degradation rate of catalysts represented by sample numbers 1 to 7.

FIG. 2 is a graph that shows a relationship between heat treatment conditions and the toluene decomposition rate of the organic matter decomposition catalysts represented by sample numbers 1 to 7. FIG. 3 is a graph that shows a relationship between heat treatment conditions and the BET specific surface area (SSA) of the organic matter decomposition catalysts represented by sample numbers 1 to 7, and FIG. 4 is a graph that shows a relationship between the BET specific surface area (SSA) and the toluene decomposition rate. FIG. 5 is a graph that shows a relationship between the Ba content rate x and the degradation rate of the organic matter decomposition catalysts represented by sample numbers 1 to 7.

As shown in FIG. 2, the toluene decomposition rates of the organic matter decomposition catalysts represented by sample numbers 3 to 7, which satisfy the requirements of the present invention, did not decrease so much and retained high values even after the high temperature heat treatment at 1200° C. or more. In contrast, the toluene decomposition rates of the organic matter decomposition catalysts represented by sample numbers 1 and 2, which do not satisfy the requirements of the present invention, largely decreased after the high temperature heat treatment at 1200° C. or more, and the toluene decomposition rates were lower than 80% especially after the high temperature heat treatment at 1400° C. or more.

It is known that the specific surface area of a catalytic powder generally decreases after a high temperature heat treatment (see FIG. 3), so that the toluene decomposition rate also decreases. By checking the relationship between the specific surface area of the catalytic powder and the toluene decomposition rate, however, concerning the organic matter decomposition catalysts represented by sample numbers 3 to 7 that have a Ba content rate x of 1.001 or more, it was revealed that even when the specific surface area decreases, the toluene decomposition rate does not decrease so much as shown in FIG. 4. Meanwhile, in the case of the organic matter decomposition catalysts represented by sample numbers 1 and 2 that have a Ba content rate x of 1.000 or less and do not satisfy the requirements of the present invention, along with a decrease in the specific surface area, the toluene decomposition rate largely decreased. The reason is presumably that in the case of the organic matter decomposition catalyst that satisfies the requirements of the present invention, the decrease in the number of the active sites is suppressed even when the specific surface area decreases.

It is preferred that the specific surface area be 6 $m^2/g$ or more because the toluene decomposition rate is high as shown in FIG. 4.

As shown in FIG. 5, when the Ba content rate x was 1.001 or more, the degradation rate was 4.2% or less, whereas when the Ba content rate x was 1.000 or less, which does not satisfy the requirements of the present invention, the degradation rate was 13.8% or more. It is especially preferred that the Ba content rate x be 1.005 or more because a degradation rate of 1.9% or less is achieved.

Among the organic matter decomposition catalysts represented by sample numbers 3 to 7 that satisfy the requirements of the present invention, the organic matter decomposition catalysts represented by sample numbers 3 to 6 satisfy the relationships of $1.001 \leq x \leq 1.05$ and $0.05 \leq z \leq 0.2$. These catalysts had toluene decomposition rates of 93.3% or more before the high temperature heat treatment. In contrast, the organic matter decomposition catalyst represented by sample number 7 that does not satisfy the relationships had a toluene decomposition rate as low as 87.5% before the high temperature heat treatment.

Figure 6:
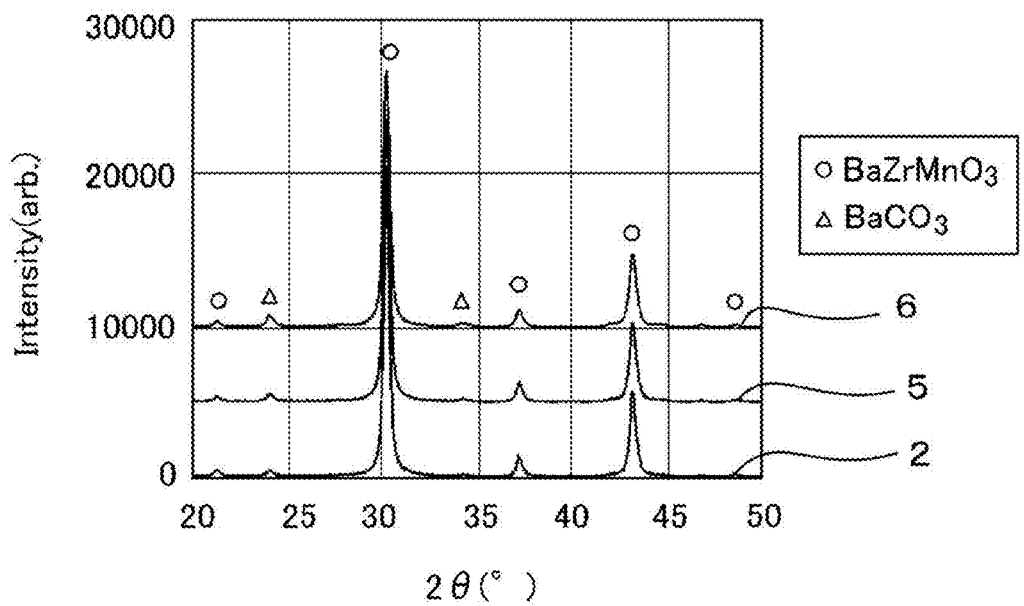
FIG. 6 is a graph that shows analysis results by X-ray diffractometry of powders of catalysts represented by sample numbers 2, 5, and 6 before a high temperature heat treatment.

The organic matter decomposition catalysts represented by sample numbers 2, 5, and 6 were finely ground with a mortar before the high temperature heat treatment, and the resulting powders were analyzed by X-ray diffractometry. FIG. 6 is a graph that shows analysis results by X-ray diffractometry. As shown in FIG. 6, it was confirmed that the main component of the organic matter decomposition catalysts was a perovskite type complex oxide that is $BaZrMnO_3$.

The organic matter decomposition catalyst represented by sample number 5 was finely ground with a mortar before the high temperature heat treatment, and the composition analysis of the resulting powder was performed by X-ray fluorescence analysis (XRF analysis). A quantitative analysis was performed using a fundamental parameter method. The standard sample used in the quantitative analysis was the powder that was obtained in the aforementioned step in which the perovskite type complex oxide was produced to produce the organic matter decomposition catalyst represented by sample number 5, that is, the powder that was obtained by drying the slurry by a dryer. The quantitative analysis results are shown in Table 2.

TABLE 2

| Sample | XRF analysis results | | |
|---|---|---|---|
| number | Ba (x) | Zr (y) | Mn (z) |
| 5 | 1.010 | 0.900 | 0.100 |

It is understood from Table 2 that the organic matter decomposition catalyst having the desired composition was obtained.

The organic matter decomposition catalysts represented by sample numbers 8 to 11 contain a perovskite type complex oxide represented by $A_xB_yM_zO_w$, wherein A is Ba, B is Zr, M is Mn, x=1.001, and the numbers of z are different from each other while the relationship of y+z=1.0 is satisfied. As shown in Table 1, the organic matter decomposition catalysts represented by sample numbers 8 to 10 that satisfy the requirements of the present invention have low degradation rates compared with the organic matter decomposition catalyst represented by sample number 11 that does not satisfy the requirements of the present invention.

Among the organic matter decomposition catalysts represented by sample numbers 8 to 10 that satisfy the requirements of the present invention, the organic matter decomposition catalyst represented by sample number 8 does not satisfy the relationships of $1.001 \leq x \leq 1.05$ and $0.05 \leq z \leq 0.2$. This catalyst had a low toluene decomposition rate before the high temperature heat treatment compared with the organic matter decomposition catalysts represented by sample numbers 9 and 10 that satisfy the relationships of $1.001 \leq x \leq 1.05$ and $0.05 \leq z \leq 0.2$.

The organic matter decomposition catalysts represented by sample numbers 12 to 15 contain a perovskite type complex oxide represented by $A_xB_yM_zO_w$, wherein A is Ba, B is Zr, M is Mn, x=1.050, and the numbers of z are different from each other while the relationship of y+z=1.0 is satisfied. As shown in Table 1, the organic matter decomposition catalysts represented by sample numbers 12 to 14 that satisfy the requirements of the present invention have low degradation rates compared with the organic matter decomposition catalyst represented by sample number 15 that does not satisfy the requirements of the present invention.

Among the organic matter decomposition catalysts represented by sample numbers 12 to 14 that satisfy the requirements of the present invention, the catalyst represented by sample number 12 does not satisfy the relationships of $1.001 \leq x \leq 1.05$ and $0.05 \leq z \leq 0.2$. This catalyst had a low toluene decomposition rate before the high temperature heat treatment compared with the organic matter decomposition catalysts represented by sample numbers 13 and 14 that satisfy the relationships of $1.001 \leq x \leq 1.05$ and $0.05 \leq z \leq 0.2$.

The organic matter decomposition catalysts represented by sample numbers 16 to 20 contain a perovskite type complex oxide represented by $A_xB_yM_zO_w$, wherein A is Ba, B is Zr, and M is Co. As shown in Table 1, the organic matter decomposition catalysts represented by sample numbers 17 to 19 that satisfy the requirements of the present invention have high toluene decomposition rates and low degradation rates even after the high temperature heat treatment at 1400° C. compared with the organic matter decomposition catalysts represented by sample numbers 16 and 20 that do not satisfy the requirements of the present invention.

The organic matter decomposition catalysts represented by sample numbers 21 to 25 contain a perovskite type complex oxide represented by $A_xB_yM_zO_w$, wherein A is Ba, B is Zr, and M is Mn, Co, Ni, and Fe. As shown in Table 1, the organic matter decomposition catalysts represented by sample numbers 22 to 24 that satisfy the requirements of the present invention have low degradation rates compared with the organic matter decomposition catalysts represented by sample numbers 21 and 25 that do not satisfy the requirements of the present invention.

The organic matter decomposition catalysts represented by sample numbers 26 to 30 contain a perovskite type complex oxide represented by $A_xB_yM_zO_w$, wherein A is Sr, B is Zr, and M is Mn. As shown in Table 1, the organic matter decomposition catalysts represented by sample numbers 27 to 29 that satisfy the requirements of the present invention have low degradation rates compared with the organic matter decomposition catalysts represented by sample numbers 26 and 30 that do not satisfy the requirements of the present invention.

The organic matter decomposition catalysts represented by sample numbers 31 to 35 contain a perovskite type complex oxide represented by $A_xB_yM_zO_w$, wherein A contains Ba and Sr, B is Zr, and M is Mn, Co, Ni, and Fe. As shown in Table 1, the organic matter decomposition catalysts represented by sample numbers 32 to 34 that satisfy the requirements of the present invention have low degradation rates compared with the organic matter decomposition catalysts represented by sample numbers 31 and 35 that do not satisfy the requirements of the present invention.

Figure 7:
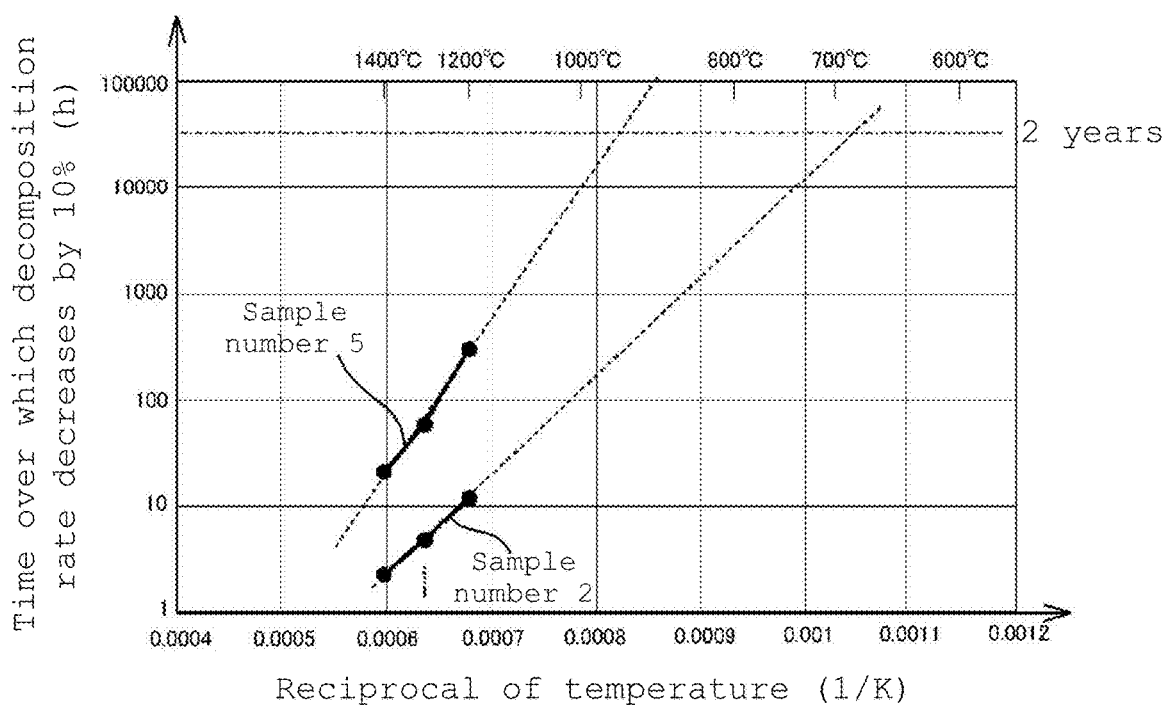
FIG. 7 is a graph that shows a relationship between a reciprocal of the temperature of the heat treatment and the time required for the toluene decomposition rate to decrease by 10% by the heat treatment.

Here, with reference to FIG. 7, concerning the organic matter decomposition catalysts represented by sample numbers 2 and 5, the relationship is considered between the temperature of the heat treatment and the time required for the toluene decomposition rate before the heat treatment to decrease by 10% after the heat treatment. In FIG. 7, the horizontal axis shows the reciprocal of the temperature of the heat treatment, and the vertical axis shows the time required for the toluene decomposition rate to decrease by 10% by the heat treatment. The vertical axis is logarithmic.

As shown in FIG. 7, when the toluene decomposition rate of the organic matter decomposition catalyst represented by sample number 2 that does not satisfy the requirements of the present invention decreases by 10% by a heat treatment over 2 years, the temperature is lower than 700° C. That is, when the organic matter decomposition catalyst represented by sample number 2 that does not satisfy the requirements of the present invention is continuously subjected to the heat treatment at 700° C., the toluene decomposition rate decreases by 10% in a shorter period than 2 years, that is, the general life of a catalyst.

On the other hand, when the toluene decomposition rate of the organic matter decomposition catalyst represented by sample number 5 that satisfies the requirements of the present invention decreases by 10% by a heat treatment over 2 years, the temperature is higher than 900° C. That is, the toluene decomposition rate of the organic matter decomposition catalyst represented by sample number 5 that satisfies the requirements of the present invention decreases by less than 10% not only when the organic matter decomposition catalyst undergoes the heat treatment at 700° C. for 2 years but also when the organic matter decomposition catalyst undergoes a heat treatment at 900° C. for 2 years.

As aforementioned, the organic matter decomposition catalyst that satisfies the requirements of the present invention has a high toluene decomposition rate and minimal heat degradation even when the organic matter decomposition catalyst undergoes the heat treatment at a high temperature, for example, a temperature higher than 1000° C. In particular, the degradation rate represented by formula (2) is less than 10%, and the organic matter decomposition catalyst has good heat resistance. In addition, the degradation can be suppressed even after a heat treatment for a long period, for example, after a heat treatment at 700° C. for 2 years.

An organic matter decomposition catalyst that satisfies the requirements of the present invention and the relationships about x and z of $x < 1.1$ and $z > 0.02$ is more preferable as a heat resistant catalyst than an organic matter decomposition catalyst that does not satisfy the aforementioned relationships about x and z because the former has a higher toluene decomposition rate before the high temperature heat treatment.

An organic matter decomposition catalyst that satisfies the requirements of the present invention and the relationships about x and z of $1.001 \leq x \leq 1.05$ and $0.05 \leq z \leq 0.2$ is more preferable as a heat resistant catalyst than an organic matter decomposition catalyst that does not satisfy the aforementioned relationships about x and z because the former has a higher toluene decomposition rate before the high temperature heat treatment.

Example 2

High purity powders of $Ag_2O$, $CaCO_3$, $Y_2O_3$, $La(OH)_3$, $Lu_2O_3$, $MgCO_3$, $ZnO$, $Al_2O_3$, $Ga_2O_3$, $Sc_2O_3$, $In_2O_3$, $GeO_2$, $TiO_2$, $HfO_2$, $SnO_2$, $Nb_2O_5$, and $Ta_2O_5$ were prepared in addition to the high purity powders of $BaCO_3$, $SrCO_3$, $ZrO_2$, $MnCO_3$, $Co_3O_4$, $NiO$, and $Fe_2O_3$ used in Example 1. The powders were weighed so as to have the composition shown in Table 3, pure water was added to the resulting mixture, and the mixture was wet-mixed with a $ZrO_2$ boulder to obtain a slurry. The slurry was dried with a dryer at 120° C., and then the resulting powder was heat-treated under the conditions of 1100° C. for 2 hours to obtain a target perovskite type complex oxide.

The resulting perovskite type complex oxide, to which an organic binder and pure water were added, was wet-mixed with a $ZrO_2$ boulder to obtain a slurry. The slurry was dried with a dryer at 120° C. and then ground. After that, the resulting matter was molded using a compression molding machine into a cylinder having a diameter of 8.5 mm and a thickness of 8 mm.

The resulting molded body was fired under the conditions of 1050° C. for 2 hours and then ground with a mortar and classified to obtain a particulate organic matter decomposition catalyst having a size of 0.5 mm or more and 0.6 mm or less.

A part of the resulting organic matter decomposition catalyst was subjected to a high temperature heat treatment in an electric furnace under the conditions of 1400° C. for 3 hours.

By the aforementioned steps, organic matter decomposition catalysts before and after the high temperature heat treatment, the catalysts respectively having compositions represented by sample numbers 36 to 52 shown in Table 3, were obtained. Then, the toluene decomposition rates were determined before and after the high temperature heat treatment, and the degradation rates were calculated in the same manner as in Example 1.

The elements that A contains in the range of 10 at % or less are not limited to the aforementioned at least one element selected from the group consisting of Ag, Ca, Y, La, and Lu. That is, A may contain different elements as impurities or substitutes as long as the degradation rate does not deteriorate. Because the aforementioned elements generally

TABLE 3

| | Charge composition ratio | | | | A(x) | | | | | | | B(y) | | | | |
|---|---|---|---|---|---|---|---|---|---|---|---|---|---|---|---|---|
| Smpl # | x | y | z | y + z | Ba | Sr | Ag | Ca | Y | La | Lu | Zr | Mg | Zn | Al | Ga |
| 36 | 1.010 | 0.900 | 0.100 | 1.000 | 0.990 | | 0.010 | | | | | 1.000 | | | | |
| 37 | 1.010 | 0.900 | 0.100 | 1.000 | 0.450 | 0.450 | | 0.100 | | | | 1.000 | | | | |
| 38 | 1.010 | 0.900 | 0.100 | 1.000 | 0.950 | | | | 0.050 | | | 1.000 | | | | |
| 39 | 1.010 | 0.900 | 0.100 | 1.000 | 0.900 | | 0.050 | | | 0.050 | | 1.000 | | | | |
| 40 | 1.010 | 0.900 | 0.100 | 1.000 | 0.990 | | | | | | 0.010 | 1.000 | | | | |
| 41 | 1.010 | 0.900 | 0.100 | 1.000 | 1.000 | | | | | | | 0.990 | 0.010 | | | |
| 42 | 1.010 | 0.900 | 0.100 | 1.000 | 1.000 | | | | | | | 0.990 | | 0.010 | | |
| 43 | 1.010 | 0.900 | 0.100 | 1.000 | 1.000 | | | | | | | 0.990 | | | 0.010 | |
| 44 | 1.010 | 0.900 | 0.100 | 1.000 | 1.000 | | | | | | | 0.990 | | | | 0.010 |
| 45 | 1.010 | 0.900 | 0.100 | 1.000 | 0.500 | 0.500 | | | | | | 0.990 | | | | |
| 46 | 1.010 | 0.900 | 0.100 | 1.000 | 1.000 | | | | | | | 0.990 | | | | |
| 47 | 1.010 | 0.900 | 0.100 | 1.000 | 1.000 | | | | | | | 0.990 | | | | |
| 48 | 1.010 | 0.900 | 0.100 | 1.000 | 0.500 | 0.500 | | | | | | 0.950 | | | | |
| 49 | 1.010 | 0.900 | 0.100 | 1.000 | 1.000 | | | | | | | 0.800 | | | | |
| 50 | 1.010 | 0.900 | 0.100 | 1.000 | 1.000 | | | | | | | 0.900 | | | | |
| 51 | 1.010 | 0.900 | 0.100 | 1.000 | 1.000 | | | | | | | 0.980 | | | | |
| 52 | 1.010 | 0.900 | 0.100 | 1.000 | 1.000 | | | | | | | 0.900 | | | | 0.050 |

| | B(y) | | | | | | | M(z) | Toluene decomp rate (%) | | Degr. Rate |
|---|---|---|---|---|---|---|---|---|---|---|---|
| Smpl # | Sc | In | Ge | Ti | Hf | Sn | Nb | Ta | Mn | Bf high temp | 1400° C./3 h | (%) |
| 36 | | | | | | | | | 1.000 | 93.2 | 91.8 | 1.5 |
| 37 | | | | | | | | | 1.000 | 94.3 | 92.7 | 1.7 |
| 38 | | | | | | | | | 1.000 | 94.2 | 92.5 | 1.8 |
| 39 | | | | | | | | | 1.000 | 93.9 | 92.0 | 2.0 |
| 40 | | | | | | | | | 1.000 | 92.1 | 90.5 | 1.7 |
| 41 | | | | | | | | | 1.000 | 94.5 | 93.1 | 1.5 |
| 42 | | | | | | | | | 1.000 | 91.9 | 90.2 | 1.8 |
| 43 | | | | | | | | | 1.000 | 92.1 | 90.8 | 1.4 |
| 44 | | | | | | | | | 1.000 | 90.8 | 89.7 | 1.2 |
| 45 | 0.010 | | | | | | | | 1.000 | 93.5 | 91.8 | 1.8 |
| 46 | | 0.010 | | | | | | | 1.000 | 91.2 | 89.8 | 1.5 |
| 47 | | | 0.010 | | | | | | 1.000 | 90.3 | 88.9 | 1.6 |
| 48 | | | | 0.050 | | | | | 1.000 | 93.4 | 91.5 | 2.1 |
| 49 | | | | | 0.200 | | | | 1.000 | 94.1 | 92.6 | 1.6 |
| 50 | | | | | | 0.100 | | | 1.000 | 93.7 | 91.9 | 1.9 |
| 51 | | | | | | | 0.010 | 0.010 | 1.000 | 93.3 | 92.3 | 1.1 |
| 52 | | | | | | | | 0.050 | 1.000 | 93.6 | 92.2 | 1.5 |

The organic matter decomposition catalysts represented by sample numbers 36 to 52 shown in Table 3 are the catalysts that satisfy the requirements of the present invention.

The organic matter decomposition catalysts represented by sample numbers 36 to 40 have a structure in which a part of Ba in the perovskite type complex oxide that is contained in the organic matter decomposition catalyst represented by sample number 5 is substituted with at least one element selected from the group consisting of Sr, Ag, Ca, Y, La, and Lu. However, A in the perovskite type complex oxide represented by $A_xB_yM_zO_w$ contains 90 at % or more of at least one element selected from the group consisting of Ba and Sr.

As shown in Table 3, even when A contains at least one element selected from the group consisting of Ag, Ca, Y, La, and Lu in a range of 10 at % or less, the toluene decomposition rates were high after the high temperature heat treatment at 1400° C., and the degradation rates were as low as 2.0% or less.

have an ionic valence as in $Ag^+$, $Ca^{2+}$, $Y^{3+}$, $La^{3+}$, and $Lu^{3+}$ and the ions have a six-coordination ionic radius in a range of 0.86 Å to 1.15 Å (see Table 4), examples of the different elements or ions that A can contain include elements or ions that have a six-coordination ionic radius in the range of 0.86 Å to 1.15 Å.

TABLE 4

| Presence site of ion | Ionic species | Ionic radius (Å) |
|---|---|---|
| A | Ba2+ | 1.35 |
| | Sr2+ | 1.18 |
| | Ca2+ | 1.00 |
| | Y3+ | 0.90 |
| | La3+ | 1.03 |
| | Lu3+ | 0.86 |
| | Ag+ | 1.15 |
| B | Zr4+ | 0.72 |
| | Mg2+ | 0.72 |
| | Zn2+ | 0.74 |

TABLE 4-continued

| Presence site of ion | Ionic species | Ionic radius (Å) |
|---|---|---|
| | Al3+ | 0.54 |
| | Ga3+ | 0.62 |
| | Sc3+ | 0.75 |
| | In3+ | 0.80 |
| | Ge4+ | 0.53 |
| | Ti4+ | 0.61 |
| | Hf4+ | 0.71 |
| | Sn4+ | 0.69 |
| | Nb5+ | 0.64 |
| | Ta5+ | 0.64 |

The catalysts represented by sample numbers 41 to 52 have a structure in which a part of Zr in the perovskite type complex oxide that is contained in the catalyst represented by sample number 5 is substituted with at least one element selected from the group consisting of Mg, Zn, Al, Ga, Sc, In, Ge, Ti, Hf, Sn, Nb, and Ta in a range of 20 at % or less. That is, B in the perovskite type complex oxide represented by $A_xB_yM_zO_w$ contains 80 at % or more of Zr and at least one element selected from the group consisting of Mg, Zn, Al, Ga, Sc, In, Ge, Ti, Hf, Sn, Nb, and Ta.

As shown in Table 3, even when B contains at least one element selected from the group consisting of Mg, Zn, Al, Ga, Sc, In, Ge, Ti, Hf, Sn, Nb, and Ta in a range of 20 at % or less in addition to 80 at % or more of Zr, the toluene decomposition rates were high after the high temperature heat treatment at 1400° C., and the degradation rates were as low as 2.1% or less.

The elements that B contains in the range of 20 at % or less are not limited to the aforementioned at least one element selected from the group consisting of Mg, Zn, Al, Ga, Sc, In, Ge, Ti, Hf, Sn, Nb, and Ta. That is, A may contain different elements as impurities or substitutes as long as the degradation rate does not deteriorate. Because the aforementioned elements generally have an ionic valence as in $Mg^{2+}$, $Zn^{2+}$, $Al^{3+}$, $Ga^{3+}$, $Sc^{3+}$, $In^{3+}$, $Ge^4$, $Ti^{4+}$, $Hf^{4+}$, $Sn^{4+}$, $Nb^{5+}$, and $Ta^{5+}$ and the ions have a six-coordination ionic radius in a range of 0.53 Å to 0.80 Å (see Table 4), examples of the different elements or ions that B can contain include elements or ions that have a six-coordination ionic radius in the range of 0.53 Å to 0.80 Å.

As aforementioned, also in Example 2, the organic matter decomposition catalyst that satisfies the requirements of the present invention has a high toluene decomposition rate even when the organic matter decomposition catalyst undergoes the heat treatment at a high temperature, for example, a temperature higher than 1000° C. In particular, the degradation rate represented by formula (2) is less than 2.1%, that is, the heat degradation is minimized, and the organic matter decomposition catalyst has good heat resistance.

The present invention is not to be considered limited to the embodiment described above, but various applications and modifications can be made within the scope of the invention. For example, although it is described that the control unit 3 controls the heating unit 2 so that the area heated by the heating unit 2 may have a temperature of 700° C. or more and 1500° C. or less, the controlled temperature is not limited to the aforementioned temperature. That is, the temperature of the environment in which the organic matter decomposition catalyst according to the present invention is used is not limited to the range of 700° C. or more and 1500° C. or less.

DESCRIPTION OF REFERENCE SYMBOLS

1: Tube
2: Heating unit
3: Control unit
4: Gas supply tube
5: Gas exhaust tube
10: Test apparatus
41: Toluene supply line
42: Nitrogen supply line
43: Oxygen supply line
51: Sampling line

The invention claimed is:

1. An organic matter decomposition catalyst comprising: a perovskite type complex oxide represented by $A_xB_yM_zO_w$, wherein A contains 90 at % or more of at least one element selected from the group consisting of Ba and Sr, B contains 80 at % or more of Zr, M is at least one element selected from the group consisting of Mn, Co, Ni, and Fe, $y+z=1$, $x>1$, $z<0.4$, and w is a positive value that satisfies electrical neutrality.

2. The organic matter decomposition catalyst according to claim 1, wherein $x<1.1$.

3. The organic matter decomposition catalyst according to claim 1, wherein $z>0.02$.

4. The organic matter decomposition catalyst according to claim 1, wherein $1.001 \leq x \leq 1.05$ and $0.05 \leq z \leq 0.02$.

5. The organic matter decomposition catalyst according to claim 1, wherein A further contains at least one element selected from the group consisting of Y, La, Lu, Ca, and Ag.

6. The organic matter decomposition catalyst according to claim 5, wherein B further contains at least one element selected from the group consisting of Mg, Zn, Al, Ga, Sc, In, Ge, Ti, Hf, Sn, Nb, and Ta.

7. The organic matter decomposition catalyst according to claim 1, wherein B further contains at least one element selected from the group consisting of Mg, Zn, Al, Ga, Sc, In, Ge, Ti, Hf, Sn, Nb, and Ta.

8. The organic matter decomposition catalyst according to claim 1, wherein A further contains at least one element or ion that has a six-coordination ionic radius in a range of 0.86 Å to 1.15 Å.

9. The organic matter decomposition catalyst according to claim 8, wherein B further contains at least one element or ion that has a six-coordination ionic radius in a range of 0.53 Å to 0.80 Å.

10. The organic matter decomposition catalyst according to claim 1, wherein B further contains at least one element or ion that has a six-coordination ionic radius in a range of 0.53 Å to 0.80 Å.

11. An organic matter decomposition aggregate comprising an aggregate of the organic matter decomposition catalyst according to claim 1, the aggregate having a specific surface area of 6 m²/g or more.

12. The organic matter decomposition aggregate according to claim 11, wherein $x \geq 1.005$.

13. The organic matter decomposition aggregate according to claim 11, wherein A of the organic matter decomposition catalyst further contains at least one element selected from the group consisting of Y, La, Lu, Ca, and Ag.

14. The organic matter decomposition aggregate according to claim 13, wherein B of the organic matter decomposition catalyst further contains at least one element selected from the group consisting of Mg, Zn, Al, Ga, Sc, In, Ge, Ti, Hf, Sn, Nb, and Ta.

15. The organic matter decomposition aggregate according to claim 11, wherein B of the organic matter decomposition catalyst further contains at least one element selected from the group consisting of Mg, Zn, Al, Ga, Sc, In, Ge, Ti, Hf, Sn, Nb, and Ta.

16. An organic matter decomposition apparatus comprising:
   a tube in which an organic matter flows;
   a heating unit that heats the organic matter flowing in the tube;
   a control unit that controls the heating unit; and
   the organic matter decomposition aggregate according to claim 11 inside the tube in an area heated by the heating unit.

17. The organic matter decomposition apparatus according to claim 16, wherein the control unit controls the heating unit so that the area heated by the heating unit has a temperature of 700° C. or more.

18. The organic matter decomposition apparatus according to claim 16, wherein the control unit controls the heating unit so that the organic matter decomposition aggregate has a temperature of 700° C. or more.

19. The organic matter decomposition apparatus according to claim 16, wherein the control unit controls the heating unit so that the organic matter decomposition aggregate has a temperature of 1500° C. or less.

* * * * *